United States Patent [19]
Hirsch et al.

[11] Patent Number: 4,946,835
[45] Date of Patent: Aug. 7, 1990

[54] ANTIFUNGAL FERMENTATION PRODUCT AND METHOD

[75] Inventors: Charles F. Hirsch, Sommerville; Jerrold M. Liesch, Princeton Junction; Michael J. Salvatore, South Plainfield; Robert E. Schwartz; David F. Sesin, both of Westfield, all of N.J.

[73] Assignee: Merck & Co., Inc., Rahway, N.J.

[21] Appl. No.: 219,942

[22] Filed: Jul. 15, 1988

[51] Int. Cl.$^5$ .................. A61K 31/395; C07D 273/08
[52] U.S. Cl. .................................. 514/183; 540/454; 435/118; 435/120; 435/252.2
[58] Field of Search ..................... 540/454; 514/183

[56] References Cited

U.S. PATENT DOCUMENTS 4,341,533  2/1983  Akimoto et al. ................ 540/462

OTHER PUBLICATIONS

Kupchan, S. M. et al., J. Am. Chem. Soc. 94:4, 1354 (1972).

Primary Examiner—Robert T. Bond
Attorney, Agent, or Firm—Alice O. Robertson; Michael C. Sudol, Jr.

[57] ABSTRACT

A novel dioxa-diazacyclohexadecenetetrone isolated from the fermentation of a cyanobacterium (Nostoc sp.) is described. The compound is a new antifungal agent with a specificity generally toward filamentous fungi but also effective against Cryptococcus sp.

6 Claims, 1 Drawing Sheet

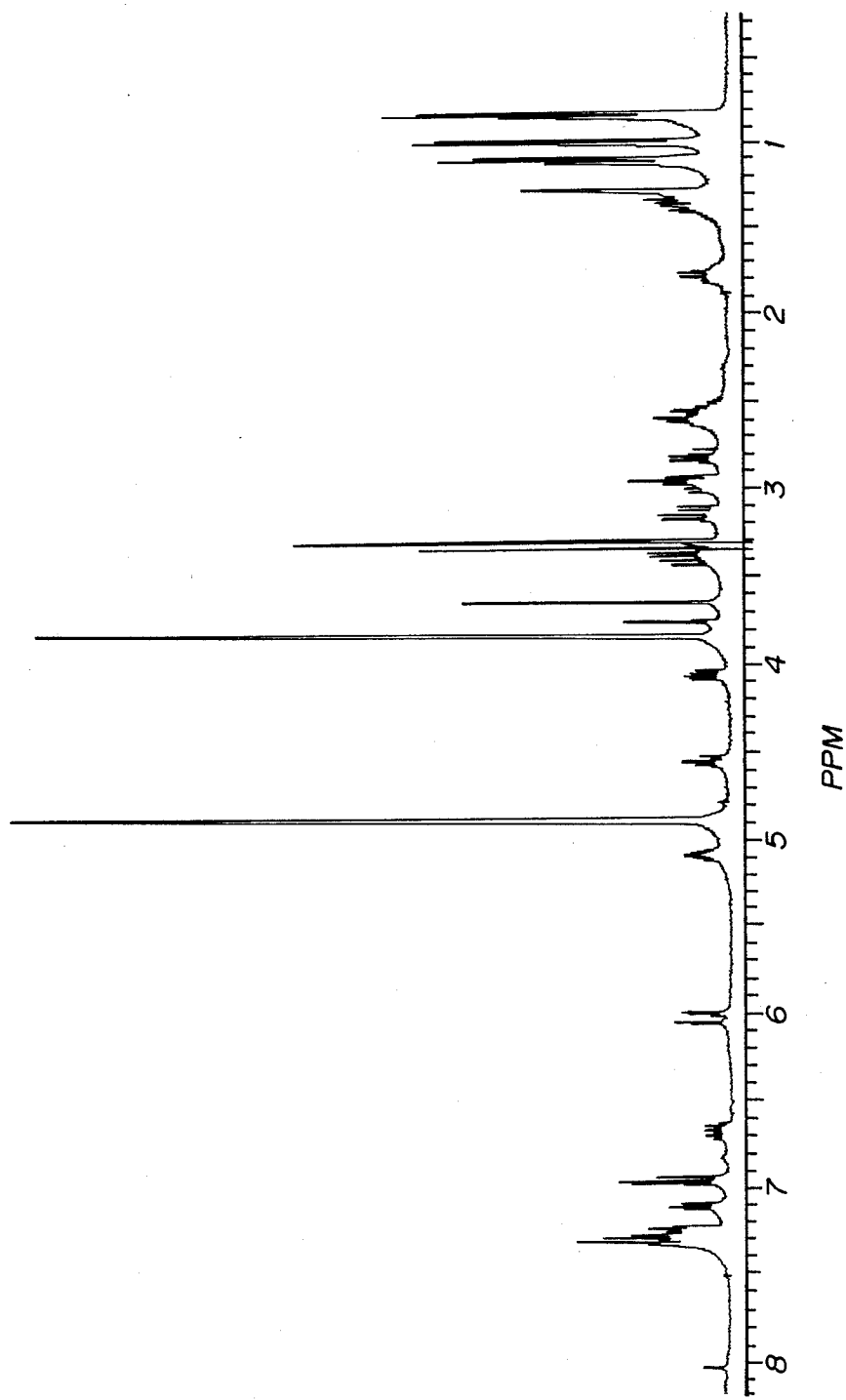

ANTIFUNGAL FERMENTATION PRODUCT AND METHOD

DESCRIPTION OF THE INVENTION

The present invention is directed to a new antifungal fermentation product isolated from a previously undescribed strain of cyanobacterium (Nostoc species) which shows good activity against filamentous fungi and also against certain yeast organisms, especially the Cryptococcus species. Thus, the invention embraces controlling fungal growth including mycotic infections. It is also directed to a method of producing the compound and to the producing organism.

The novel antifungal agent is a light colored solid which is believed to be a dioxa-diazacyclohexadecenetetrone compound represented by the following formula:

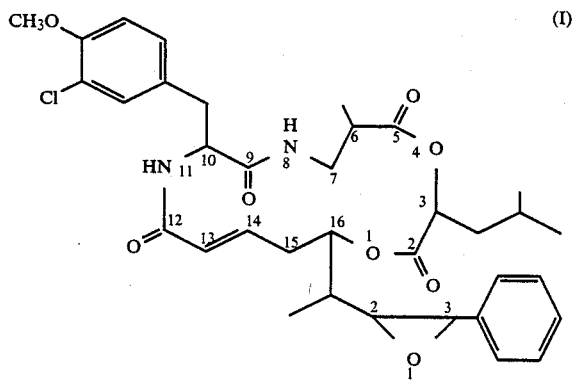

The compound may be identified by the Chemical Abstracts nomenclature of 10-[(3-chloro 4methoxyphenyl)methyl]-6-methyl-3-(2-methylpropyl)-16-[1-(3-phenyloxiranyl)ethyl]-1,4-dioxa-8,11-diazacyclohexadec-13-ene-2,5,9,12-tetrone. For convenience, the compound hereinafter shall be referred to as Compound I.

Compound I may be characterized by the following physical properties:

Mass Spectral Data

The molecular formula of this compound is $C_{35}H_{43}N_2O_8Cl$ (calc 654.2708; found 654.2697) by high resolution mass spectrometry (HR-MS). Critical fragment ions are observed at m/z 412, 394, 280, 244, 227, 195 and 155. The four subunits which comprise the total structure can be characterized from the four compounds observed in the total acid hydrolysate of the parent molecule by the gas chromatogram mass spectra of the trimethylsilyl derivative:
(1) bis-silyl beta aminoisobutyric acid;
(2) bis-silyl alpha-hydroxyisovaleric acid;
(3) bis-silyl-(chloro, methoxy)phenylalanine (calc for $[C_{10}H_{12}ClNO_3+(SiC_3H_8)_2-CH_3]358.1062$; found 358.1062); and
(4) bis-silyl-7,8-epoxy-5-hydroxy-6-methyl-8-phenyloctene-2-oic acid (calc for $[C_{15}H_{18}O_4+(SiC_3H_8)_2-CH_3]391.1761$; found 391.1775).

Infrared Spectral Data

The IR spectrum of the neat compound is as seen in FIG. 1.

NMR Spectral Data $^{13}C$ NMR chemical shifts obtained in $CD_3OD$ at 75 MHz are as follows: 177.48, 174.04, 172.22, 168.26, 155.33, 143.25, 138.63, 132.19, 131.49, 129.75(2C), 129.51, 129.31, 126.91(2C), 125.56, 123.22, 113.47, 77.73, 72.60, 64.45, 60.11, 57.45, 56.59, 41.74, 41.11, 40.63, 38.99, 38.56, 36.35, 25.61, 23.29, 21.65, 15.12, 14.03.

$^1H$ NMR spectrum in $CD_3OD$ at 300 MHz is as seen in FIG. 2.

The antibiotic compound of the present invention identified by formula I is a white or light colored glassy solid, soluble in organic solvents and adaptable to be employed in solution. It is also adaptable to be employed in aqueous dispersions.

The novel antibiotic is active against filamentous fungi and certain yeasts, particularly the Cryptococcus species. It is especially useful in the treatment of fungi caused diseases such as aspergilliosis which are of concern in immune compromised patients although not generally of concern in persons in normal health. It is also useful for the control of fungi which are allergens, or plant pathogens, or which cause rot or other deterioration in paints, textiles, wood, wood products, paper products and the like. The compound while active broadly against filamentous fungi, is especially effective against Aspergillus species, such as *Aspergillus niger, Aspergillus flavus* and *Aspergillus fumiqatus; Alternaria solani*; Penicillium species; *Cochliobolus miyabeanus*; Phoma species; *Botrytis allii; Ceratocystis ulmi; Fusarium oxysporum*, and others. The compound is also active against certain bacteria species such as Erwinia species, Staphylococcus species; and Serratia species The antibiotic antifungal agent of the present invention may be produced by cultivating an unidentified strain of Nostoc sp., designated MB 5357 in the culture collection of Merck and Co., Rahway, N.J. and recovering said compound from the culture broth. A sample of the culture, capable of producing the compounds has been deposited under the Budapest Treaty in the culture collection of the American Type Culture Collection at 12301 Parklawn Drive, Rockville, Md. 20852. The sample has been assigned the accession Number ATCC 53789.

The morphological and cultural characteristics of MB 5357 are as follows:

A. Morpholoqical Characteristics

Microscopic examination shows that the vegetative cells are spherical, ovoid, or cylindrical and occur in filaments. In longer filaments, heterocysts occasionally are observed in an intercalary position. Akinetes have not been observed. Reproduction is by hormogonia in addition to random trichome breakage.

B. Culture Characteristics

Growth on agar. (BG-13 medium at 25° C., about 3000 lux and 5 percent (volume/volume) carbon dioxide in air) is flat, filamentous, opaque and pigmented dark green and the culture excretes a faint yellow brown soluble pigment.

The culture tolerates storage at −80° C. (10% glycerol cryoprotectant) for at least 3 months.

A careful comparison of the foregoing data with the published descriptions in a publication by R. Rippka et al., "Generic assignments, strain histories and properties of pure cultures of cyanobacteria," J. Gen. Microbiol 111, 1–61 (1979), indicates that the organism appears to be a member of typological group IV in the genus Nostoc, as defined by Rippka et al.

Although the invention is explained hereinbelow principally with respect to the specific strain, it is well known in the art that the properties of microorganisms may be varied naturally and artificially. Thus, all strains of the genus Nostoc, ATCC 53789, including variants and mutants, whether obtained by natural selection, produced by the action of mutating agents such as ionizing radiation or ultraviolet irradiation, or by the action of chemical mutagens such as nitrosoguanidine, are contemplated and employable in the invention.

The antibiotic of this invention is produced during aerobic fermentation of a medium hereinafter described with a producing strain of Nostoc MB 5357 and thereafter recovering the active component from the fermentation medium.

For producing the compound of the present invention, a seed culture is first prepared from a preserved culture of the producing organism and thereafter regrown through a multistep procedure. The medium most suitable for producing the antibiotic is the BG-13 medium.

| BG-13 MEDIUM | |
|---|---|
| Component | g/L |
| $NaNO_3$ | 1.5 |
| $NaHCO_3$ | 1.7 |
| $K_2HPO_4$ | 0.031 |
| $MgSO_4.7H_2O$ | 0.075 |
| $CaCl_2.H_2O$ | 0.036 |
| Citric acid | 0.006 |
| Ferric ammonium citrate | 0.006 |
| EDTA ($Na_2Mg$ salt) | 0.001 |
| $Na_2CO_3$ | 0.02 |
| Trace metal mix (see below) | 1 ml |
| Distilled $H_2O$ | to 1000 ml |
| pH 7.6 | |

| Trace Metal Mix | |
|---|---|
| Component | g/L* |
| $H_3BO_3$ | 2.86 |
| $MnCl_2.4H_2O$ | 1.81 |
| $ZnSO_4.7H_2O$ | 0.222 |
| $Na_2MoO_4.2H_2O$ | 0.390 |
| $CuSO_4.5H_2O$ | 0.079 |
| $CoCl_2.6H_2O$ | 0.040 |

*prepared in 0.1N HCl

The medium components modified in the following manner also provide suitable nutrient medium:

| Component | Concentration Range (g/L) |
|---|---|
| $NaNO_3$ | 1.5–3.0 |
| $K_2HPO_4$ | 0.031–0.34 |
| Sulfate | 0.075*–0.14** |

*as $MgSO_4.7H_2O$
**as $Na_2SO_4$

The seed culture is prepared by inoculating BG-13 broth with cells taken from a BG-13 agar slant culture and incubating the broth in an atmosphere of 5 percent (volume/volume) of carbon dioxide in air at temperatures in the range of from about 25° C. to about 30° C., preferably 25° C., with shaking and illuminated continuously at ~5000 lux. Agitation may be up to about 200 rpm but is preferably, lower, e.g. about 100 rpm. The headspace of the glass culture vessel is continuously flushed with gas. The incubation is carried out over a period of 16 to 25 days, preferably 20 days.

The cells from the seed culture are then used to carry out a second stage fermentation, employing similar conditions but generally a shorter time to harvest, about 12 to 18 days, preferably about 16 days. During this stage, the headspace of the vessel is flushed continuously with gas at a flow rate of about 25 milliliters per minute and the cells are kept suspended, preferably with a magnetic stirring bar operating at about 100 rpm. The cells are then harvested by centrifugation and resuspended in BG-13 medium; the suspension is employed to inoculate a culture medium, which then is incubated for a similar period to produce the desired antibiotic compound (Compound I).

The desired antibiotic compound (Compound I) may be recovered from either the cellular material or the liquid broth of the fermentation medium or from both. When the fermentation period is about two weeks, most of the material is still in the cells and recovery may be made from the cells. After a longer time, the cells lyse and then recovery is preferably from the broth although recovery may be made from both.

For carrying out the recovery after completion of the fermentation, the fermentation medium is either centrifuged to obtain cellular material and supernatant, or filtered to obtain cellular material and filtrate. The cellular material is extracted by stirring overnight with methanol and the methanolic extract is then subjected to an appropriate high pressure liquid chromatography (HPLC) assay to determine the presence of and extent of the active component. Existence of antifungal activity in the methanol extract and in the filtered broth (or supernatant) may be detected by plating with *Aspergillus niger*. Depending on the results of the assay, isolation is carried out from either the cellular extract, the liquid broth or from both components.

Recovery of Compound I from the methanol extract may be carried out by first adding water (about 10 percent by volume) to the methanol solution, thoroughly mixing, and thereafter partitioning with a halohydrocarbon solvent, preferably methylene chloride. An amount of methylene chloride about equal to the aqueous methanol is added in two to three portions and the methylene chloride layer thereafter recovered. Activity against *Aspergillus niger* may be checked at this point. The methylene chloride solution is concentrated to obtain a residue of crude product and the residue then chromatographed on a reverse phase column, employing methanol/water (75:25) as eluant at a flow rate of about 4–5 milliliters per minute. The fractions are then checked for activity and the rich cuts combined. The volatiles are then removed therefrom by subjecting the combined fractions to reduced pressure to obtain the desired product as residue. The residue may be purified by chromatography, preferably on a preparative HPLC column.

In carrying out the HPLC separation, the residue is dissolved in methanol and loaded on a column packed with commercial reverse phase resin. The column is operated using acetonitrile/water (60:40 or optionally other ratios) at 800–2000 psi which produces a flow rate of about 20 ml/min. Separation is monitored at 210 nm. Further purification may be carried out using analytical HPLC also with acetonitrile/water, preferably at 60/40, as eluant.

Recovery of Compound I from the filtered broth (or supernatant) may be carried out by partitioning the broth with about an equal total volume of ethyl acetate in about three portions, combining the ethyl acetate solutions and subjecting to reduced pressure to remove the volatiles and to recover the crude product as residue. The residue is chromatographed on a preparative HPLC column. The fractions are checked for activity in the manner previously described and the rich fractions combined; the volatiles then are removed in vacuo and the resulting residue chromatographed on a preparative HPLC column using 60/40 acetonitrile/water as eluant. Further purification, if desired, may be carried out using analytical HPLC.

The broad antifungal activity of Compound I against fungi may be illustrated with representative assay results in a disk diffusion assay. Filamentous fungi used in the assays were prepared from stock cultures which had been maintained on potato dextrose agar (Difco) and transferred serially at two week intervals using standard microbiological techniques. Yeast used were prepared from stock cultures of strains of yeast which had been maintained frozen at −80° C. in 20 percent aqueous glycerol.

Seeded agar assay plates were prepared according to the type of assay strain. Inoculum for filamentous fungi was prepared by scraping the surface of stock plates with a moistened sterile dacron swab. The spores and mycelia were then suspended in 10 milliliters of sterile potato dextrose broth (PDB) and adjusted to 70% transmittance (T) at 660 nm. Inoculum for Cryptococcus was prepared from overnight broth cultures. Cultures were then diluted into PDB to a final concentration of either 40% or 70% T at 660 nm. Assay plates were prepared by diluting the inoculum into appropriate molten agar medium, and thereafter cooled to 45° C., to yield a final concentration of 4 percent.

Samples were applied to 6.2 mm filter paper disks (25 μl disk) and air dried at 24° C. The disks were then applied to seed assay plates with sterile forceps, and rewetted with sterile 25 percent aqueous dimethyl sulfoxide (DMSO). The assay plates were then incubated at either 28° C. or 37° C. for 24 hours.

Following incubation, inhibition zones were measured and recorded. Measurements were made from the extreme edge of a zone where the growth differed from the background lawn. Inhibition zones were further qualified as follows: fuzzy (F)—a zone that had a fuzzy edge and clear center surrounding the disc, hazy (H)—a zone that was hazy throughout, slightly hazy (S)—a zone in which low levels of growth were discernible throughout the inhibition zone, and very hazy (V)—a zone in which the differences between the background lawn and inhibition zone were barely discernible. Zones without a qualifier were those which were clear throughout. Representative results are seen in the following table.

TABLE

| Fungal Species | Zone (Millimeters) |
|---|---|
| Alternaria solani | 21S |
| Aspergillus flavus | 21S |
| Aspergillus fumigatus | 17S |
| Aspergillus niger | 24S |
| Aspergillus niger | 21S |
| Botrytis allii | 20S |
| Cephalosporium sp. | 16V |
| Ceratocystis ulmi | 18S |
| Cercospora beticola | 15S |
| Cochliobolus miyabeanus | 23F |
| Fusarium oxysporum | 19F |
| Penicillium sp. | 24S |
| Penicillium sp. | 23F |
| Penicillium sp. | 23S |
| Phoma sp. | 22S |
| Rhizomucor miehei | 12V |

TABLE-continued

| Fungal Species | Zone (Millimeters) |
|---|---|
| Scopulariopsis communes | 13H |
| Trichoderma lignorum | 10S |
| Trichoderma sp. | 14S |
| Ustilago zea | 10S |
| Verticillium serrae | 11V |
| Cryptococcus albidus | 14S |
| Cryptococcus laurentii | 15H |
| Cryptococcus laurentii | 13H |
| Cryptococcus laurentii | 14S |

The antibiotic Compound I also showed superior potential as a therapeutic agent against mycotic infection caused by pathogens such as the Cryptococcus species.

Such activity may be illustrated with test results against Cryptococcus neoformans employing yeast nitrogen base dextrose agar medium. In carrying out the assay, Compound I was solubilized in 10 percent dimethyl sulfoxide (DMSO) supplemented with one drop of Tween 20. Twofold dilutions were made with sterile distilled water/10 percent DMSO to obtain final drug concentrations in the agar dilution assay plates ranging from 128 to 0.06 μg/ml against two strains of Cryptococcus neoformans and subsequently against an expanded panel of 84 Cryptococcus strains at concentrations ranging from 0.008 to 16.0 μg/ml.

Nystatin or amphotericin B was used as a positive control. For the assay, nystatin was solubilized in 10 percent dimethylformamide and diluted in sterile distilled water; amphotericin B was solubilized by expressing water directly into a lyophilized cake and shaking until the colloidal solution was clear and then diluted in sterile distilled water. The final drug concentrations ranged from 0.063 to 128 μg/ml.

The minimum inhibitory concentration (MIC) against the organisms employed on the standard assay were as follows:

| Fungal species | Strain | Minimum Inhibitory Concentration μg/ml | |
|---|---|---|---|
| | | Compound I | Nystatin |
| Cryptococcus neoformans | MY1051 | ≦0.063 | 1.0 |
| Cryptococcus neoformans | MY1146 | ≦0.063 | 1.0 |

The results against the expanded panel of 84 Cyptococcus neoformans isolates were as follows:

| | Activity (μg/ml) | |
|---|---|---|
| | Compound I | Amphotericin B |
| G-MIC[a] | 0.03 | <0.16 |
| Range | ≦0.008−>16.0 | ≦0.063−0.25 |
| MIC$_{50}$[b] | 0.031 | 0.125 |
| MIC$_{90}$[c] | 0.031 | 0.25 |

[a] geometric means of MIC
[b] concentration at which 50% of the strains were inhibited
[c] concentration at which 90% of the strains were inhibited The antifungal properties of the present invention may be effectively utilized by administering an antifungal amount of Compound I to the area, object or subject on or in which control of fungi is desired. The amount of Compound I to be employed depends on the particular fungal organism to be controlled and the particular environment in which it is to be administered.

The antifungal properties are most effectively utilized when Compound I is formulated into antifungal treating compositions with a biologically inert carrier which in cases of use in pharmaceutical applications should also be pharmaceutically acceptable.

The compositions are formulated according to conventional compounding techniques with a biologically inert carrier, generally with the aid of a surface active dispersing agent, the nature of which would vary depending on whether the use is for the control of pathogens infecting man or animals, or for control of fungi in agriculture such as in soil or plant parts, or for the control of fungi in or on inanimate objects.

The novel compositions preferably contain 5 percent or more by weight of the active compound and, if a concentrate composition, may contain 15 percent or more. In preparing the compositions, Compound I is intimately admixed with an appropriate carrier.

For non-therapeutic applications, the product of the present invention, either singly or as a mixture, may be employed in compositions in an inert carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

For therapeutic applications, the product of the present invention may be employed in compositions employing a carrier suitable for therapeutic application. Such carriers include liquids such as water, glycol, oil, alcohols and the like which may include buffering agents, sodium chloride, dextrose and various suspending, stabilizing, solubilizing or dispersing agents. Solid carriers include starches, sugars, kaolin, ethyl cellulose, calcium carbonate, sodium carbonate, calcium phosphate, kaolin, talc, lactose, lubricants such as calcium stearate, binders, disintegrating agents and the like.

Compound I may be used in topical application. For such applications, the drug may be formulated in conventional creams and ointments such as white petrolatum, anhydrous lanolin, cetyl alcohol, cold cream, glyceryl monostearate, rose water and the like. Usually a 5 percent cream or solution is prepared and applied to the area to be treated.

The antifungal compositions may be employed by applying to the area where fungal control is desired in such amounts as necessary to effect the desired control.

The following examples illustrate the invention but are not to be construed as limiting.

EXAMPLE I 25 milliliters of a 20 day seed culture containing cells of the cyanobacterium of the genus Nostoc were used to inoculate 1 liter of growth culture of BG-13 medium (pH 7.6) and the culture incubated at 25° C. at a light intensity of 5000 lux under a continuously replenished atmosphere of 5 percent (volume/volume) carbon dioxide in air. The headspace of the 1000 milliliter glass culture vessel was continuously flushed with gas at a flow rate of 25 milliliters/minute and the cells were kept suspended using a magnetic stirrer operating at about 100 rpm. At the end of 16 days, the cells were harvested for recovery of the desired fermentation product.

EXAMPLE II

Scaled up regrowths of the culture were carried out in the following manner:

Cells from an agar slant culture of Nostoc species were inoculated in 50 milliliters of BG-13 medium and incubated for 11 days at 25° C. at a light intensity of 5000 lux under a continuously replenished atmosphere of 5 percent (volume/volume) carbon dioxide in air at a flow rate of 25 milliliters per minute. At the end of this period, the cells were transferred into 200 milliliters of BG-13 medium and the resulting medium incubated for 13 days under the same conditions of light, temperature and atmosphere. At the end of this period, the medium was centrifuged, the cells harvested and the cells resuspended in 40 milliliters of BG-13 medium. 10 milliliter portions of this cell suspended culture were used to inoculate four media each consisting of 1 liter of BG-13 medium. The media were then incubated for 12 days under conditions previously described to obtain the desired fermentation product.

EXAMPLE III

Fermentation

A tube containing cells of MB 5357 frozen at $-80°$ C. in 10 milliters of 10 percent (w/v) glycerol was thawed, the glycerol aseptically washed from the cells by centrifugation, and the cells inoculated in 1 liter of BG-13 medium. The inoculated culture was incubated at 25° C. under a continuously replenished atmosphere of 5 percent (v/v) carbon dioxide in air and continuously illuminated at 5,000 lux using cool-white fluorescent lamps.

On the seventh day, the entire volume of the 1 liter culture was used to inoculate 10 liters of sterile BG-13 medium supplemented with 1 mM $Na_2SO_4$ and 2 mM $K_2HPO_4$. The culture was incubated at 21°-23° C. under a continuously replenished atmosphere of 5 percent (v/v) carbon dioxide in air and continuously illuminated at 16,000 lux with cool-white fluorescent lamps.

On the ninth day the light intensity was increased to 25,000 lux.

On the eighteenth day, the fermentation was terminated and the fermentation medium vacuum filtered through Whatman #1 filter paper to obtain cellular material and filtered broth.

Isolation

Isolation from cells. The cells on the filter were extracted by stirring overnight and with about 1 liter of methanol. About 200 milliliters of water was added to the methanol extract of the cells and the resulting aqueous methanol solution was partitioned with two 500 milliliter portions of methylene chloride. Tests of the methylene chloride solutions indicated presence of an agent active against *Aspergillus niger*. The methylene chloride solutions were combined and concentrated to obtain a residue and the latter chromatographed on a reverse phase LiChroprep RP-18 column (24 mm×30 cm) employing methanol/water (75:25) as eluant at a flow rate of 4–5 milliliters per minute and collecting 28 milliter fractions. Activity was detected in fraction 12–22; the active cuts were combined and the volatiles removed in vacuo to obtain 46 milligrams of a purified glassy solid. It was subsequently chromatographed on a Prep HPLC RP-18 column (Zorbax ODS-3 (siliceous microparticulate porous particles, DuPont) 21.2 mm×25 cm) using 60/40 acetonitrile/water as eluant at a flow rate of 20 milliliters/minute. The active fractions were collected and combined and the volatiles removed to obtain 16 milligrams of Compound I having the spectral properties previously detailed.

Isolation from broth. The filtered broth of the 11 liter fermentation batch was partitioned with 10–12 liters of ethyl acetate (three times with 3–4 liters of ethyl acetate each time) to concentrate the active portion (against *Aspergillus niger*) in the ethyl acetate. The volatiles were removed from the ethyl acetate solution in vacuo and the residue chromatographed on a HPLC Prep RP-18 column using 75/25 methanol/water as eluant. The active cuts were then combined and the volatiles removed in vacuo to obtain 7.2 milligrams of Compound I having the spectral properties previously set forth.

ISOLATION OF PRODUCING ORGANISM

The producing microorganism was originally isolated from an enrichment culture established with a lichen sample obtained from Arron Island, Scotland. To establish the enrichment culture, a piece (about 3 square millimeters) of the lichen thallus was placed into 2.5 milliliters of BG-13 medium and incubated at 25° C. under an atmosphere of 5 percent (v/v) carbon dioxide in air and continuous illumination (about 5000 lux). After 3 to 4 weeks incubation, growth of an alga was observed in the enrichment culture and the alga was subsequently isolated into a pure culture of Nostoc MB5357, ATCC 53789 and maintained as a BG-13 agar slant.

What is claimed is:
1. A compound represented by the formula

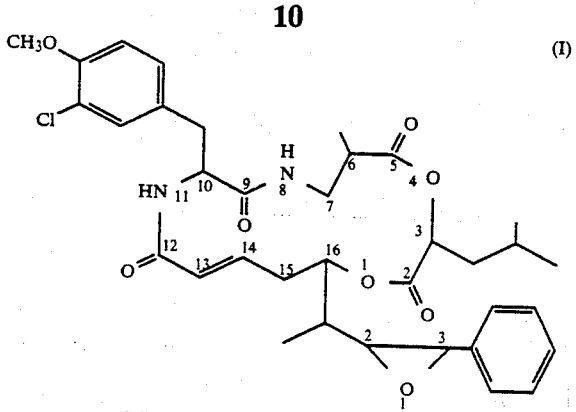

2. An antifungal composition which comprises at least 5 percent by weight of a compound of claim 1 in admixture with a biologically inert carrier.

3. A composition according to claim 2 in which the carrier is a pharmaceutically acceptable carrier.

4. A method for controlling fungal growth comprising administering to an area where growth is to be controlled, an antifungally effective amount of the compound of claim 1.

5. A method for controlling mycotic infections which comprises administering to an animal infected with fungi, an antifungally effective amount of the compound of claim 1.

6. 10-[(3-chloro-4-methoxyphenyl)methyl]-6-methyl-3-(2-methylpropyl)-16-[1-(3-phenyloxiranyl)ethyl]-1,4-dioxa-8,11-diazacyclohexadec-13-ene-2,5,9,12-tetrone produced by cultivating a strain of MB 5357, ATCC 53,89 in an aqueous nutrient medium.

* * * * *